United States Patent
Köhler

(10) Patent No.: US 10,698,052 B2
(45) Date of Patent: Jun. 30, 2020

(54) INTERPOLATED THREE-DIMENSIONAL THERMAL DOSE ESTIMATES USING MAGNETIC RESONANCE IMAGING

(71) Applicant: KONINKLIJKE PHILIPS N.V., Eindhoven (NL)

(72) Inventor: Max Oskar Köhler, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 1309 days.

(21) Appl. No.: 14/385,247

(22) PCT Filed: Mar. 5, 2013

(86) PCT No.: PCT/IB2013/051726
§ 371 (c)(1),
(2) Date: Sep. 15, 2014

(87) PCT Pub. No.: WO2013/140284
PCT Pub. Date: Sep. 26, 2013

(65) Prior Publication Data
US 2015/0038828 A1 Feb. 5, 2015

Related U.S. Application Data

(60) Provisional application No. 61/614,031, filed on Mar. 22, 2012.

(30) Foreign Application Priority Data

Mar. 22, 2012 (EP) ..................... 12160778

(51) Int. Cl.
A61B 5/055 (2006.01)
G01R 33/48 (2006.01)
(Continued)

(52) U.S. Cl.
CPC .......... *G01R 33/4804* (2013.01); *A61B 5/015* (2013.01); *A61B 5/055* (2013.01);
(Continued)

(58) Field of Classification Search
None
See application file for complete search history.

(56) References Cited

U.S. PATENT DOCUMENTS 4,674,046 A 6/1987 Ozeki
4,983,921 A 1/1991 Kramer et al.
(Continued)

OTHER PUBLICATIONS

Mougenot, C. et al "Quantification of Near-Field Heating During Volumetric MR_HIFU Ablation", Medical Physics, vol. 38, No. 1, Dec. 2010, pp. 272-282.
(Continued)

*Primary Examiner* — Jonathan Cwern

(57) ABSTRACT

The invention provides for a medical apparatus (400, 500, 600, 700, 800) comprising a magnetic resonance imaging system (402) for acquiring magnetic resonance thermometry data (442) from a subject (418). The magnetic resonance imaging system comprises a magnet (404) with an imaging zone (408). The medical apparatus further comprises a memory (432) for storing machine executable instructions (460, 462, 464, 466, 10, 660). The medical apparatus further comprises a processor (426) for controlling the medical apparatus, wherein execution of the machine executable instructions causes the processor to: acquire (100, 200, 300) the magnetic resonance thermometry data from multiple slices (421, 421', 421") within the imaging zone by controlling the magnetic resonance imaging system; and interpolate (102, 202, 204, 302, 304) a three dimensional thermal dose estimate (444) in accordance with the magnetic resonance thermometry data.

15 Claims, 10 Drawing Sheets

(51) Int. Cl.
    *A61B 5/01*     (2006.01)
    *G01R 33/30*    (2006.01)
    *G01R 33/31*    (2006.01)

(52) U.S. Cl.
    CPC ............ *G01R 33/30* (2013.01); *G01R 33/31* (2013.01); *G01R 33/4814* (2013.01)

(56) References Cited

U.S. PATENT DOCUMENTS

| | | |
|---|---|---|
| 5,378,987 A | 1/1995 | Ishihara |
| 5,916,161 A | 6/1999 | Ishihara et al. |
| 6,466,814 B1 | 10/2002 | Ardenkjaer-Larsen |
| 6,522,142 B1 | 2/2003 | Freundlich |
| 6,559,644 B2 | 5/2003 | Froundlich |
| 7,772,846 B2 | 8/2010 | Roland |
| 8,030,922 B2 | 10/2011 | Roland |
| 8,159,223 B2 | 4/2012 | Luekeke et al. |
| 2010/0315084 A1 | 12/2010 | Sacolick et al. |
| 2011/0046472 A1 | 2/2011 | Schmidt |

OTHER PUBLICATIONS

Hendrick, R. Edward "Time-Saving Measures in 3D Gradient-Echo Imaging", Breast MRI—Fundamentals and Technical Aspects, Jan. 2008, pp. 151-154.

Kohler et al "Volumetric HIFU Ablation Under 3D Guidance of Rapid MRI Thermometry" Proc. Intl. Soc. Mag. Reson. Med 16 (2008) p. 66.

Li et al , "VD K-T Acquisition for Accelerating Temperature Imaging" Proc. Intls. Soc. Mag. Reson. Med. 15 92007) p. 1134.

US 10,698,052 B2

INTERPOLATED THREE-DIMENSIONAL THERMAL DOSE ESTIMATES USING MAGNETIC RESONANCE IMAGING

CROSS-REFERENCE TO PRIOR APPLICATIONS

This application is the U.S. National Phase application under 35 U.S.C. § 371 of International Application No. PCT/IB2013/051726, filed on Mar. 5, 2013, which claims the benefit of U.S. Provisional Patent Application No. 61/614,031, filed on Mar. 22, 2012 and European Patent Application No. 12160778.2, filed on Mar. 22, 2012. These applications are hereby incorporated by reference herein.

TECHNICAL FIELD

The invention relates to magnetic resonance imaging, in particular to the use of magnetic resonance imaging for the estimation of three dimensional thermal doses.

BACKGROUND OF THE INVENTION

The thermal dose is a measure of thermal tissue damage that is based on the Arrhenius equation and was originally introduced by Sapareto and Dewey in 1984 and is given by $$TD(t) = \int_0^t R^{43-T(\tau)} d\tau$$

where $$R = \begin{cases} 0.25, & T \le 43 \\ 0.5, & T > 43 \end{cases}$$

and T is the temperature. The unit is typically given in equivalent minutes at 43 degrees Celsius. An increase of one degree (when above 43 degrees) doubles the thermal dose. This measure is currently the most prominently used measure for estimating when adequate thermal damage has been obtained in thermal therapies. A conventionally used limit for thermal necrosis in muscle tissue and uterine fibroids is 240 equivalent minutes at 43 degrees, although this limit has been found to be tissue dependent as some tissues are more sensitive to increases in temperature than other. Other measures for estimating the thermal damage also exist, such as the maximum temperature (which is very similar to the thermal dose for rapid heatings) and the Arrhenius equation as such. The thermal dose is typically applied in high-intensity focused ultrasound (HIFU) treatments whereas for example laser ablation often adopts the Arrhenius equation in its original form to assess thermal damage.

Whatever the measure, they have in common that they only use the measured temperature. The temperature can be measured by thermocouples, optical fibers, MR thermometry, US thermometry, thermoacoustic sensing, or any such means. These means of measuring the temperature have in common that they only measure the temperature at some points (thermo sensors), or in some planes (thermometry imaging, thermoacoustic sensing). The measurements may also be in 3D such as for 3D MR imaging but if so then the resolution is typically low and anisotropic to allow real-time acquisition.

For instance, magnetic resonance thermometry may be used to determine either the absolute temperature of a volume or a change in temperature, depending upon the technique used. For determining the absolute temperature several magnetic resonance peaks may be measured with spectroscopic imaging techniques. Methods which measure changes in temperature are typically faster and have been used to take temperature measurements for guiding thermal treatments. For example Proton resonance frequency shift based MR thermometry may be employed to provide temperature maps in water inside the tissue during the ablation procedure for real-time feedback control of the heating process.

In high-intensity focused ultrasound (HIFU) therapy, reliable real-time temperature monitoring using e.g. Magnetic Resonance Imaging (MRI) is necessary to ensure a sufficient thermal necrosis to the target while avoiding excessive heating and damage of surrounding healthy tissues. To achieve sufficient temporal and spatial resolution, fast imaging is required preferably with a high spatial resolution while maintaining a sufficient SNR for reconstruction of reliable temperature measurements.

SUMMARY OF THE INVENTION

The invention provides for a medical apparatus, a computer program product and a method in the independent claims. Embodiments are given in the dependent claims.

A difficulty that may arise is that thermal data or images acquired, particularly by magnetic resonance imaging, may be acquired from limited volumes or have limited spatial resolution due to restrictions placed on the acquisition time. It isn't uncommon for thermal magnetic resonance data to be acquired from only a limited volume of a subject during a thermal treatment. Embodiments of the invention may provide a means of providing an estimate of a thermal dose in a region outside of where the thermal data was acquired. Yet other embodiments may provide a means of estimating the dose at resolutions that are higher than what the thermal data was acquired at.

As mentioned above, the thermal dose is a measure used for estimating the thermal damage inflicted on the target tissue in thermal therapies. The thermal dose only makes use of the temperature history and is such a noninvasive measure that can be determined as long as temperature information is available. It is commonly used as a therapeutic endpoint in thermal therapies such as high-intensity focused ultrasound (HIFU) and may be used to provide feedback on which areas are not fully treated. For Magnetic Resonance (MR) guided HIFU the temperature information is obtained in the MR slices imaged and the temperature images is obtained using one of the standard methods for translating MR property change into temperature change. For this reason the thermal dose may be estimated in the slices used for MR imaging. This may be problematic if the images are repositioned for additional sonications as no measure of the cumulative thermal dose is then possible. To circumvent this, one may make use of the symmetry of the intended heating and the natural smoothness of the temperature distribution, heat diffusion smoothens any spatially localized temperature peaks, and interpolate into a 3D space wherein the thermal dose accumulated from all sonications may be added. By doing so, one can obtain a 3D estimate of the cumulative thermal dose for the entire treatment that may be visualized in any plane using conventional multi-planar reconstruction (MPR) methods. Even though the interpolation holds several assumptions and may not be perfect, this method may nevertheless aid in determining if the treatment is complete and therefore provide a more accurate endpoint.

A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network.

'Computer memory' or 'memory' is an example of a computer-readable storage medium. Computer memory is any memory which is directly accessible to a processor. Examples of computer memory include, but are not limited to: RAM memory, registers, and register files.

'Computer storage' or 'storage' is an example of a computer-readable storage medium. Computer storage is any non-volatile computer-readable storage medium. Examples of computer storage include, but are not limited to: a hard disk drive, a USB thumb drive, a floppy drive, a smart card, a DVD, a CD-ROM, and a solid state hard drive. In some embodiments computer storage may also be computer memory or vice versa.

A 'processor' as used herein encompasses an electronic component which is able to execute a program or machine executable instruction. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. Many programs have their instructions performed by multiple processors that may be within the same computing device or which may even be distributed across multiple computing devices.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins by the antenna of a Magnetic resonance apparatus during a magnetic resonance imaging scan. A Magnetic Resonance Imaging (MRI) image is defined herein as being the reconstructed two or three dimensional visualization of anatomic data contained within the magnetic resonance imaging data. This visualization can be performed using a computer.

Magnetic resonance data may comprise the measurements of radio frequency signals emitted by atomic spins by the antenna of a Magnetic resonance apparatus during a magnetic resonance imaging scan which contains information which may be used for magnetic resonance thermometry. Magnetic resonance thermometry functions by measuring changes in temperature sensitive parameters. Examples of parameters that may be measured during magnetic resonance thermometry are: the proton resonance frequency shift, the diffusion coefficient, or changes in the T1 and/or T2 relaxation time may be used to measure the temperature using magnetic resonance. The proton resonance frequency shift is temperature dependent, because the magnetic field that individual protons, hydrogen atoms, experience depends upon the surrounding molecular structure. An increase in temperature decreases molecular screening due to the temperature affecting the hydrogen bonds. This leads to a temperature dependence of the proton resonance frequency.

The proton density depends linearly on the equilibrium magnetization. It is therefore possible to determine temperature changes using proton density weighted images.

The relaxation times T1, T2, and T2-star (sometimes written as T2*) are also temperature dependent. The reconstruction of T1, T2, and T2-star weighted images can therefore be used to construct thermal or temperature maps.

The temperature also affects the Brownian motion of molecules in an aqueous solution. Therefore pulse sequences which are able to measure diffusion coefficients such as a pulsed diffusion gradient spin echo may be used to measure temperature.

One of the most useful methods of measuring temperature using magnetic resonance is by measuring the proton resonance frequency (PRF) shift of water protons. The resonance frequency of the protons is temperature dependent. As the temperature changes in a voxel the frequency shift will cause the measured phase of the water protons to change. The temperature change between two phase images can therefore be determined. This method of determining temperature has the advantage that it is relatively fast in comparison to the other methods. The PRF method is discussed in greater detail than other methods herein. However, the methods and techniques discussed herein are also applicable to the other methods of performing thermometry with magnetic resonance imaging.

Spectroscopic magnetic resonance data is defined herein as being the recorded measurements of radio frequency signals emitted by atomic spins by the antenna of a Magnetic resonance apparatus during a magnetic resonance imaging scan which contains information which is descriptive of multiple resonance peaks.

The spectroscopic magnetic resonance data may for instance be used to perform a proton spectroscopic (PS) imaging based temperature mapping method which can produce temperature maps on absolute scale. This absolute scale temperature map may therefore be used to perform a temperature calibration. This method relies on the physical principles of water proton resonance shift temperature dependence as the proton resonance frequency method, but the acquisition method is different: the frequency shift is calculated from the magnetic resonance spectra. The shift is calculated from the position difference of the water and a reference proton peak. Protons in lipids may for example be used as reference, as their resonance frequency is known to be almost independent of temperature, while the water proton peak has linear dependence on temperature. This can be done in the voxels, where both tissue types are present. If water and lipids do not exist in the same voxel, one may try to use some other tissue type than lipids as reference. If not successful, there may be some voxels where the reference peaks, and therefore the temperature data, are not available. Interpolation and/or temperature filtering may be used to help these situations, since body temperature is normally not expected to change rapidly spatially with the highly localized temperature rise typically caused by thermal therapy being an obvious exception. The utilization of reference peaks makes the method relatively independent of field drifts or inter-scan motion. Because the scanning takes a time of at least on the order of one minute with current methods, the PS method is susceptible to intra-scan motion or temperature change during scanning. In a case where temperature is constant or temperature variation is small both in time and space, the method is able to produce useful information. For example, with the Magnetic Resonance Guided High Intensity Focused Ultrasound (MR-HIFU), the PS method can be used to provide the actual body temperature distribution before start of MR-HIFU or other temperature treatment as opposed to using a spatially homogeneous starting temperature taken as the body core temperature measured with a thermometer probe. Alternatively, the PS method can be used as a sanity check for the cumulative temperature between heat treatments outside the treatment area.

An 'ultrasound window' as used herein encompasses a window which is able to transmit ultrasonic waves or energy. Typically a thin film or membrane is used as an ultrasound window. The ultrasound window may for example be made of a thin membrane of BoPET (Biaxially-oriented polyethylene terephthalate).

In one aspect the invention provides for a medical apparatus comprising a magnetic resonance imaging system for acquiring magnetic resonance thermometry data from a subject. The magnetic resonance imaging system comprises a magnet with an imaging zone. The magnetic resonance thermometry data is acquired from the imaging zone. The medical apparatus further comprises a memory for storing machine executable instructions. The medical apparatus further comprises a processor for controlling the medical apparatus. Execution of the machine executable instructions causes the processor to acquire the magnetic resonance thermometry data from multiple slices within the imaging zone by controlling the magnetic resonance imaging system.

Magnetic resonance data or magnetic resonance thermometry data is typically acquired from volumes called voxels or from thick slab-like volumes called slices. The magnetic resonance thermometry data from a particular slice is typically represented as a two-dimensional graph or field. Execution of the machine executable instructions further causes the processor to interpolate a three-dimensional thermal dose estimate in accordance with the magnetic resonance thermometry data. This is to say the magnetic resonance thermometry data from the multiple slices is used to interpolate a three-dimensional dose estimate. This embodiment may be beneficial because this allows the estimation of the thermal dosage in regions for which magnetic resonance data was not acquired.

In some embodiments the thermal dose may be a simplification of the Arrhenius equation and using an Arrhenius equation you can get an estimate of the tissue damage based purely on the temperature time interval.

In another embodiment execution of the instructions further cause the processor to acquire the magnetic resonance thermometry data from the multiple slices at multiple time periods. Execution of the instructions further causes the processor to calculate a two-dimensional thermal dose for each of the multiple slices. The three-dimensional thermal dose estimate is interpolated using the two-dimensional thermal dose calculated for each of the multiple slices. In this embodiment magnetic resonance thermometry data is acquired for multiple slices at different time intervals. By knowing the temperature at different time intervals a thermal dose within each of the slices can be calculated. The resulting thermal dose for the multiple slices is then used to interpolate a thermal dose estimate in three-dimensional space.

In another embodiment execution of the instructions further causes the processor to acquire the magnetic resonance thermometry data from the multiple slices at multiple time periods. Execution of the instructions further causes the processor to calculate an interpolated three-dimensional temperature map for each of the multiple time periods. The three-dimensional thermal dose estimate is calculated using each interpolated three-dimensional temperature map. In this embodiment the magnetic resonance thermometry data is again acquired at multiple time intervals or periods from multiple slices. However in this embodiment for each time period a three-dimensional temperature map is made. The resulting three-dimensional temperature map is then used to directly construct the three-dimensional thermal dose estimate.

In another embodiment the three-dimensional thermal dose estimate has a higher spatial resolution than the magnetic resonance thermometry data. In some applications the magnetic resonance temperature data may be acquired using a very coarse spatial resolution so that it may be acquired more rapidly. In some instances there is a desire to know the thermal dose or at least predict the thermal dose on a higher spatial resolution than what the magnetic resonance thermometry data was acquired. This embodiment enables a reasonable estimate of the thermal dose to be calculated by interpolating the thermal dose estimate to a higher resolution than the underlying resolution of the thermal magnetic resonance data.

In another embodiment execution of the instructions causes the processor to acquire the magnetic resonance thermometry data multiple times and to interpolate the three-dimensional thermal dose estimate multiple times. Execution of the instructions further causes the processor to calculate a cumulative thermal dose estimate by summing the multiple three-dimensional thermal dose estimates. This may be useful for instance when a temperature treatment system such as a high-intensity focused ultrasound system is used to repeatedly treat or heat or cool a target zone of a subject. The thermal dose can be determined for each heating or cooling period and then summed into a cumulative three-dimensional thermal dose estimate.

The three-dimensional thermal dose estimate of individual sonications in the case of high-intensity focused ultrasound can be added for the entire session. This may provide a three-dimensional cumulative thermal dose estimate for the particular sonication session. This may be useful for clinicians or doctors to assess the effect of a particular sonication or heating or cooling treatment. A benefit of a cumulative three-dimensional thermal dose estimate may be that it provides a three-dimensional view of the region estimated to be thermally damaged during the course of the treatment session, thus providing a very useful clinical endpoint.

In another embodiment the medical apparatus further comprises a temperature control system operable for controlling the temperature within a target zone located within the imaging zone. Execution of the instructions further causes the processor to receive a treatment plan. A treatment plan as used herein comprises instructions or data which may be used to construct constructions which are useful for controlling the temperature control system. For instance in a treatment plan a physician may outline regions of a subject which the physician desires to expose to a temperature treatment. Execution of the instructions further cause the processor to control the temperature control system in accordance with the treatment plan to control the temperature within the target zone. The instructions cause the processor to acquire at least part of the magnetic resonance thermometry data when controlling the temperature control system. The temperature control system may have a controllable heating region or focal point for controllably heating the target zone. This embodiment may be beneficial because it enables the thermal dose to be determined when the temperature control system is heating or cooling the target zone.

In another embodiment execution of the instructions further causes the processor to modify the treatment plan in accordance with the three-dimensional thermal dose estimate. This may be beneficial because the temperature control system may heat or cool the target zone in alternating temperature control time periods. Having the three-dimensional thermal dose estimate available may allow the medical apparatus to avoid temperature treating regions which are not desired to be treated or to adjust the control of the temperature control system to more accurately heat or cool the target zone.

In another embodiment execution of the instructions further cause the processor to detect an endpoint condition using the three-dimensional thermal dose estimate and the treatment plan. Execution of the instructions further cause the processor to halt at least a portion of the temperature control of the target zone by sending a halt command to the temperature control system if the endpoint condition is detected. This embodiment may be beneficial because the three-dimensional thermal dose estimate may be used to predict the thermal dosage in regions which are not being measured by thermal magnetic resonance data by the magnetic resonance imaging system. This may prevent the medical apparatus from heating or cooling the target zone longer than necessary. In some embodiments the three dimensional does estimate may also be a cumulative three dimensional dose estimate constructed by summing multiple three dimensional dose estimates.

In another embodiment the target zone has a border. Execution of the instructions further causes the processor to calculate a border thermal dose within a predetermined distance from at least a portion of the border. This embodiment may be beneficial because it may help to avoid the difficulty of cooling regions which are not intended to be heated or cooled in the treatment plan.

In another embodiment the three-dimensional thermal dose estimate may be calculated within a predetermined interpolation volume. The interpolation volume comprises the treatment zone. This embodiment may be beneficial because the region of the predetermined interpolation volume may be a region where the three-dimensional thermal dose estimate may be predicted to be accurate or reasonably accurate.

The predetermined interpolation volume can be used as a mask to look at heated regions or areas adjacent to the heated regions. This may also speed up the calculation of the three-dimensional thermal dose estimate.

In another embodiment execution of the instructions further cause the processor to determine a heating center of mass using the treatment plan. The interpolated three-dimensional thermal dose estimate is interpolated at least partially using the heating center of the mass. The heating center of mass may be determined once for each period of heating.

Partial volume effects can be taken into account in some embodiments by looking where the center of mass of heating is. Determining a heating center of mass may provide a means of counteracting the partial volume effect by using the knowledge that the heating is most likely symmetrical. Taking the center of mass and heating symmetry into account may therefore, though not necessarily, help account for partial volume effects and produce a more accurate thermal dose interpolation. For example there may be other methods such as simulation and knowledge of tissue heterogeneity distribution, thermal dose distribution, or a combination of each of these. By inserting this information into the interpolation algorithm the interpolation result can in some cases be slightly improved. This for example may be fixing the spatial coordinates in the high-resolution interpolated space to coincide with the center of mask. However, local changes in the heat transfer properties of different tissue types surrounding the heating center of mass may alter or distort the symmetry thereby reducing the accuracy of this technique in some cases.

In another embodiment execution of the instructions further cause the processor to determine a heating trajectory using the treatment plan. A heating trajectory as used herein is a sequence of locations or volumes where the temperature control system heats or cools the subject. The three-dimensional thermal dose estimate is interpolated at least partially using the heating trajectory.

In some embodiments post-processing the fidelity of the three-dimensional thermal dose estimate may be beneficial. For example if the heated trajectory is circular of a certain diameter as it is in many cases you may have an extremely large deviance from a circular shape and this occurs in a region of low signal-to-noise ratio. Those voxels should be removed because they are likely erroneous due to noise.

In another embodiment a threshold of how large a deviance from the intended region of ablation that is acceptable could be set. If the signal-to-noise ratio of that region is below a certain level then one can claim with a fair amount of confidence that the dose is due to noise.

In another embodiment the temperature control system is a high-intensity focused ultrasound system.

In another embodiment the temperature control system is a radio-frequency temperature control system.

In another embodiment the temperature control system is a microwave ablation system.

In another embodiment the temperature control system is a hyperthermia therapy system. In a hyperthermia therapy system external heating sources and/or internal heating sources are laid on and/or inserted into the subject to heat the subject.

In another embodiment the temperature control system is a laser ablation system.

In another embodiment the temperature control system is an infrared ablation system.

In another embodiment the temperature control system is a cryoablation system. A cryoablation system as used herein encompasses a system which may be used to reduce the temperature of or freeze tissue of a subject.

In another aspect the invention provides for a computer program product comprising machine executable instructions for execution by a processor controlling the medical apparatus. The medical apparatus comprises a magnetic resonance imaging system for acquiring magnetic resonance thermometry data from a subject. The magnetic resonance imaging system comprises a magnet with an imaging zone. Execution of the machine executable instructions causes the processor to acquire the magnetic resonance thermometry data from multiple slices within the imaging zone by controlling the magnetic resonance imaging system. Execution of the machine executable instructions further cause the processor to interpolate a three-dimensional thermal dose estimate in accordance with the magnetic resonance thermometry data.

In another aspect the invention provides for a method of controlling a medical apparatus. The medical apparatus comprises a magnetic resonance imaging system for acquiring magnetic resonance thermometry data from a subject. The magnetic resonance imaging system comprises a magnet with an imaging zone. The method comprises the step of acquiring the magnetic resonance thermometry data from multiple slices within the imaging zone by controlling the magnetic resonance imaging system. The method further comprises the step of interpolating a three-dimensional thermal dose estimate in accordance with the magnetic resonance thermometry data.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
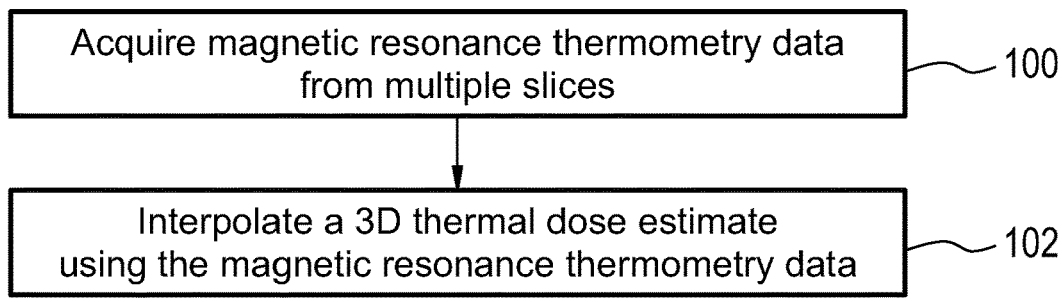
FIG. 1 shows a flow diagram which illustrates a method according to an embodiment of the invention.

FIG. 1 shows a flow diagram which illustrates a method according to an embodiment of the invention. In step 100 magnetic resonance thermometry data is acquired from multiple slices. Next in step 102 a three-dimensional thermal dose estimate is interpolated using the magnetic resonance thermometry data.

Figure 2:
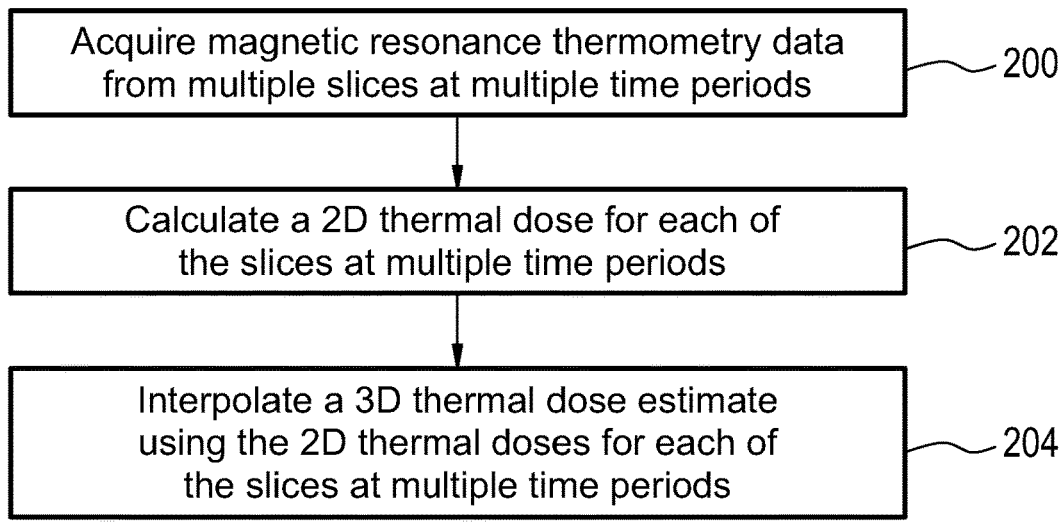
FIG. 2 shows a flow diagram which illustrates a method according to a further embodiment of the invention.

FIG. 2 shows a flow diagram which illustrates a method according to a further embodiment of the invention. In step 200 magnetic resonance thermometry data is acquired from multiple slices. Next in step 202 a thermal dose estimate is calculated for each of the slices at the multiple time periods. Next in step 204 a three-dimensional thermal dose estimate is interpolated using the two-dimensional thermal doses for each of the slices at multiple time periods.

Figure 3:
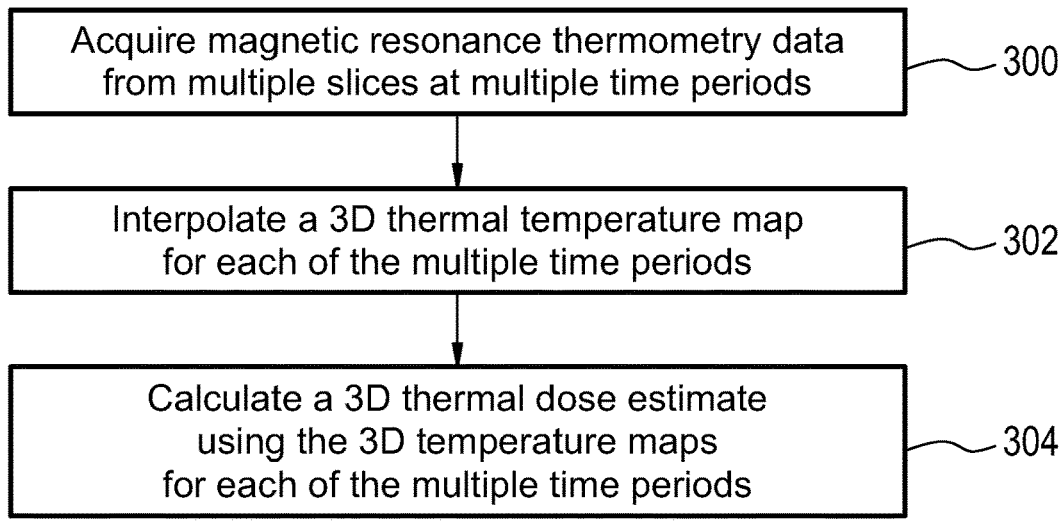
FIG. 3 shows a flow diagram which illustrates a method according to a further embodiment of the invention.

FIG. 3 shows a flow diagram which illustrates a method according to a further embodiment of the invention. First in step 300 magnetic resonance thermometry data is acquired from multiple slices at multiple time periods. Next in step 302 a three-dimensional thermal temperature map is interpolated for each of the multiple time periods. Next in step 304 a three-dimensional thermal dose estimate is calculated using the three-dimensional temperature maps for each of the multiple time periods.

Figure 4:
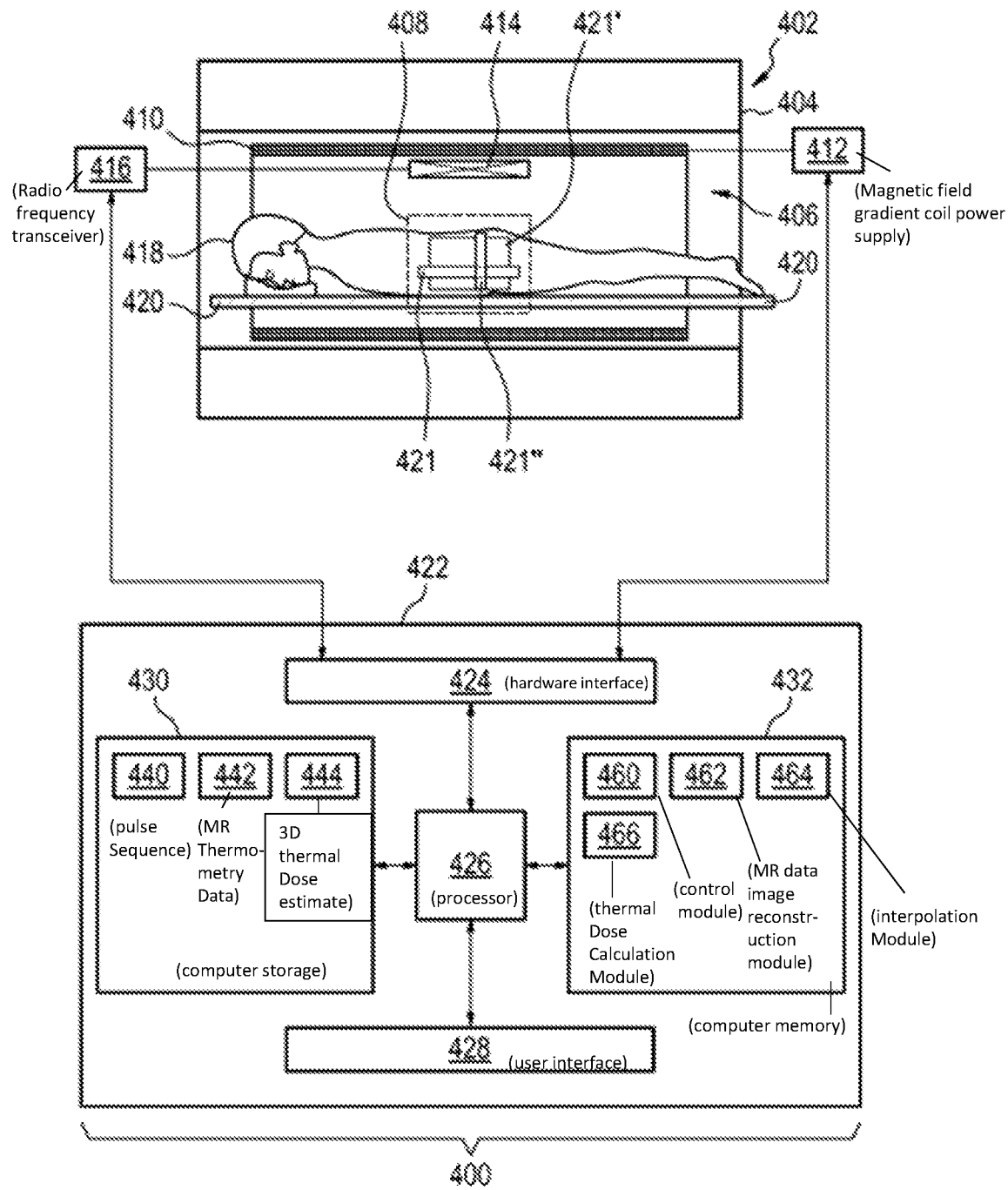
FIG. 4 illustrates a medical apparatus according to an embodiment of the invention.

FIG. 4 illustrates a medical apparatus 400 according to an embodiment of the invention. The medical apparatus 400 comprises a magnetic resonance imaging system 402. The magnetic resonance imaging system 402 is shown as comprising a magnet 404. The magnet 404 is a cylindrical type superconducting magnet with a bore 406 through the center of it. The magnet 404 has a liquid helium cooled cryostat with superconducting coils. It is also possible to use permanent or resistive magnets. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore of the cylindrical magnet there is an imaging zone 408 where the magnetic field is strong and uniform enough to perform magnetic resonance imaging.

Also within the bore of the magnet is a magnetic field gradient coil 410 which is used for acquisition of magnetic resonance data to spatially encode magnetic spins within an imaging zone of the magnet. The magnetic field gradient coil 410 is connected to a magnetic field gradient coil power supply 412. The magnetic field gradient coil is representative. Typically magnetic field gradient coils contain three separate sets of coils for spatially encoding in three orthogonal spatial directions. A magnetic field gradient power supply 412 supplies current to the magnetic field gradient coils. The current supplied to the magnetic field coils is controlled as a function of time and may be ramped and/or pulsed.

Adjacent the imaging zone 408 is a radio-frequency coil 414. The radio-frequency coil 414 is connected to a radio-frequency transceiver 416. Also within the bore of the magnet 404 is a subject 418 that is reposing on a subject support 420 and is partially within the imaging zone 408.

Adjacent to the imaging zone 408 is a radio-frequency coil 414 for manipulating the orientations of magnetic spins within the imaging zone 408 and for receiving radio transmissions from spins also within the imaging zone 408. The radio-frequency coil 414 may contain multiple coil elements. The radio-frequency coil 414 may also be referred to as a channel or an antenna. The radio-frequency coil is connected to a radio frequency transceiver 416. The radio-frequency coil 414 and radio frequency transceiver 416 may be replaced by separate transmit and receive coils and a separate transmitter and receiver. It is understood that the radio-frequency coil 414 and the radio-frequency transceiver 416 are representative. The radio-frequency coil 414 is intended to also represent a dedicated transmit antenna and a dedicated receive antenna. Likewise the transceiver 416 may also represent a separate transmitter and a separate receiver.

Within the imaging zone 408 is shown a representation of three slices 421, 421', 421". These three slices are shown as varying in different locations in three-dimensional space. Slice 421" is perpendicular to the axis of symmetry of the magnet 404. Slices 421 and 421' are perpendicular to each other and are either parallel or coplanar with the axis of symmetry of the magnet 404. The location of these slices 421, 421', 421" is intended to be representative.

The magnetic field gradient coil power supply 412 and the radio-frequency transceiver 416 are connected to a hardware interface 424 of a computer system 422. The computer system 422 further comprises a processor 426. The processor 426 is connected to the hardware interface 424. The hardware interface 424 enables the processor 426 to send and receive data and commands to the magnetic resonance imaging system 402. The computer system 422 further comprises a user interface 428, computer storage 430 and computer memory 432.

The computer memory 430 is shown as containing a pulse sequence 440 which enables magnetic resonance thermometry data 442 to be acquired from the slices 421, 421', 421". The magnetic resonance thermometry data 442 is shown as being stored in the computer storage 430. The computer storage 430 is further shown as containing a three-dimensional dose estimate 444 which was calculated using the magnetic resonance thermometry data 442.

The computer memory 432 is shown as containing a control module 460. The control module 460 contains computer executable code which enables the processor 426 to control the operation and function of the medical apparatus 400. The computer memory 432 is further shown as containing a magnetic resonance data image reconstruction module 462. The magnetic resonance data image reconstruction module 462 enables the processor 426 to reconstruct images and/or thermal maps from the magnetic resonance data and/or magnetic resonance thermometry data 442. The computer memory 432 is shown as further containing an interpolation module 464 and a thermal dose calculation module 466. The interpolation module 464 and the thermal dose calculation module 446 were used to calculate the three-dimensional thermal dose estimate 444.

Figure 5:
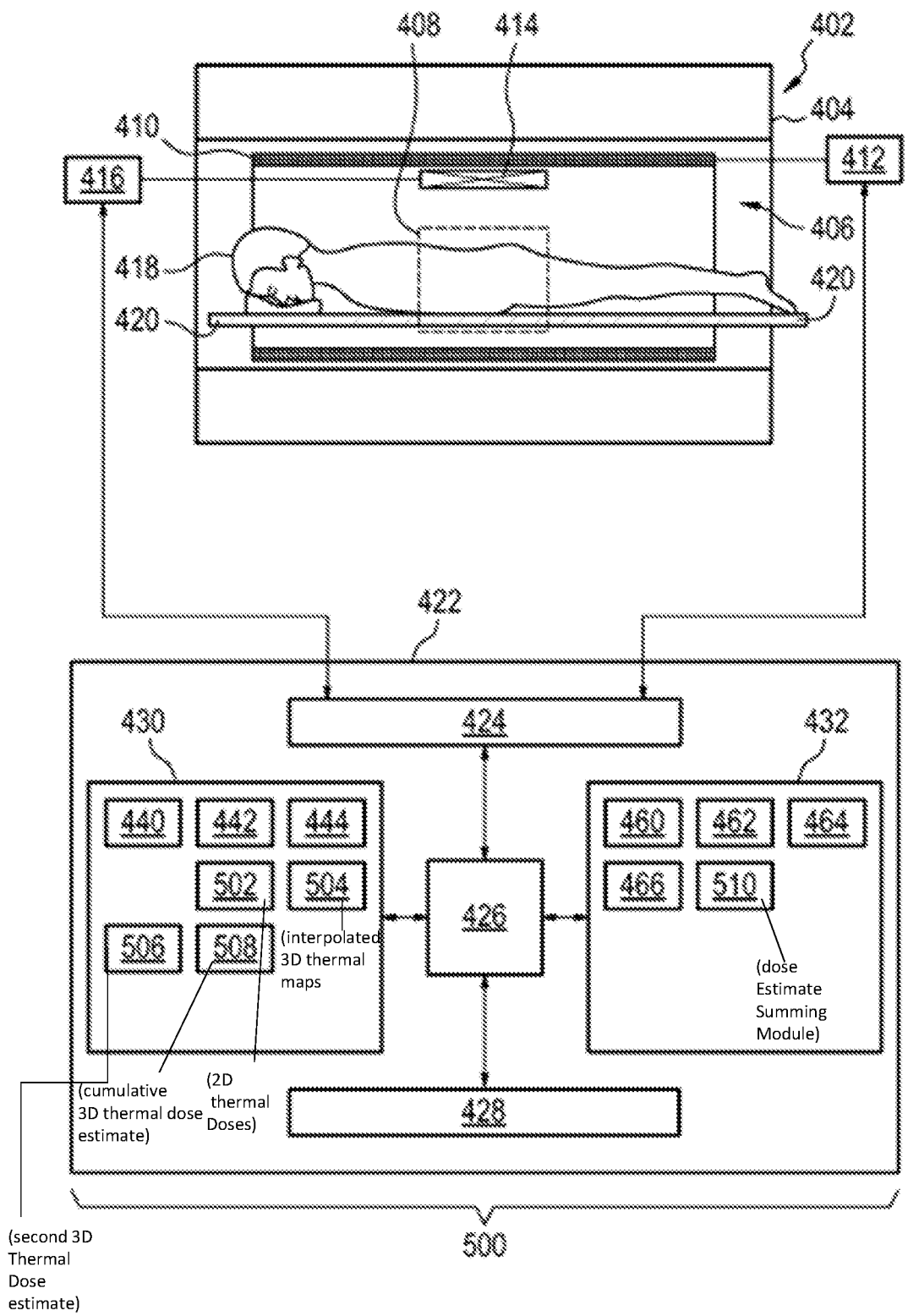
FIG. 5 illustrates a medical apparatus according to a further embodiment of the invention.

FIG. 5 shows a medical apparatus 500 according to a further embodiment of the invention. The medical apparatus 500 illustrated in FIG. 5 is similar to that of the medical apparatus 400 shown in FIG. 4. In this embodiment the computer storage 430 is further shown as containing an optional two-dimensional thermal dose calculated for the slices of the thermal magnetic resonance data 442. The computer storage 430 is shown as further containing interpolated three-dimensional thermal maps 504. The three-dimensional thermal dose estimate 444 may be calculated using the two-dimensional thermal dose estimates 502 or the interpolated three-dimensional thermal maps 504. Elements 502 and 504 may or may not be present in various embodiments. The computer storage 430 is shown as containing a second three-dimensional thermal dose estimate 506. For instance the thermal doses may be calculated at different times or from thermal magnetic resonance data that has been acquired over a period of different time intervals or times. The computer storage 430 is shown as containing a cumulative three-dimensional thermal dose estimate 508. The cumulative thermal dose estimate 508 is the three-dimensional thermal dose estimate 444 with the second three-dimensional thermal dose estimate 506.

The computer memory 432 is shown as further containing a dose estimate summing module 510. The dose estimate summing module 510 contains computer executable code which enables the processor to sum the three-dimensional thermal dose estimate 444 and the second three-dimensional thermal dose estimate 506 to obtain the cumulative three-dimensional thermal dose estimate 508.

Figure 6:
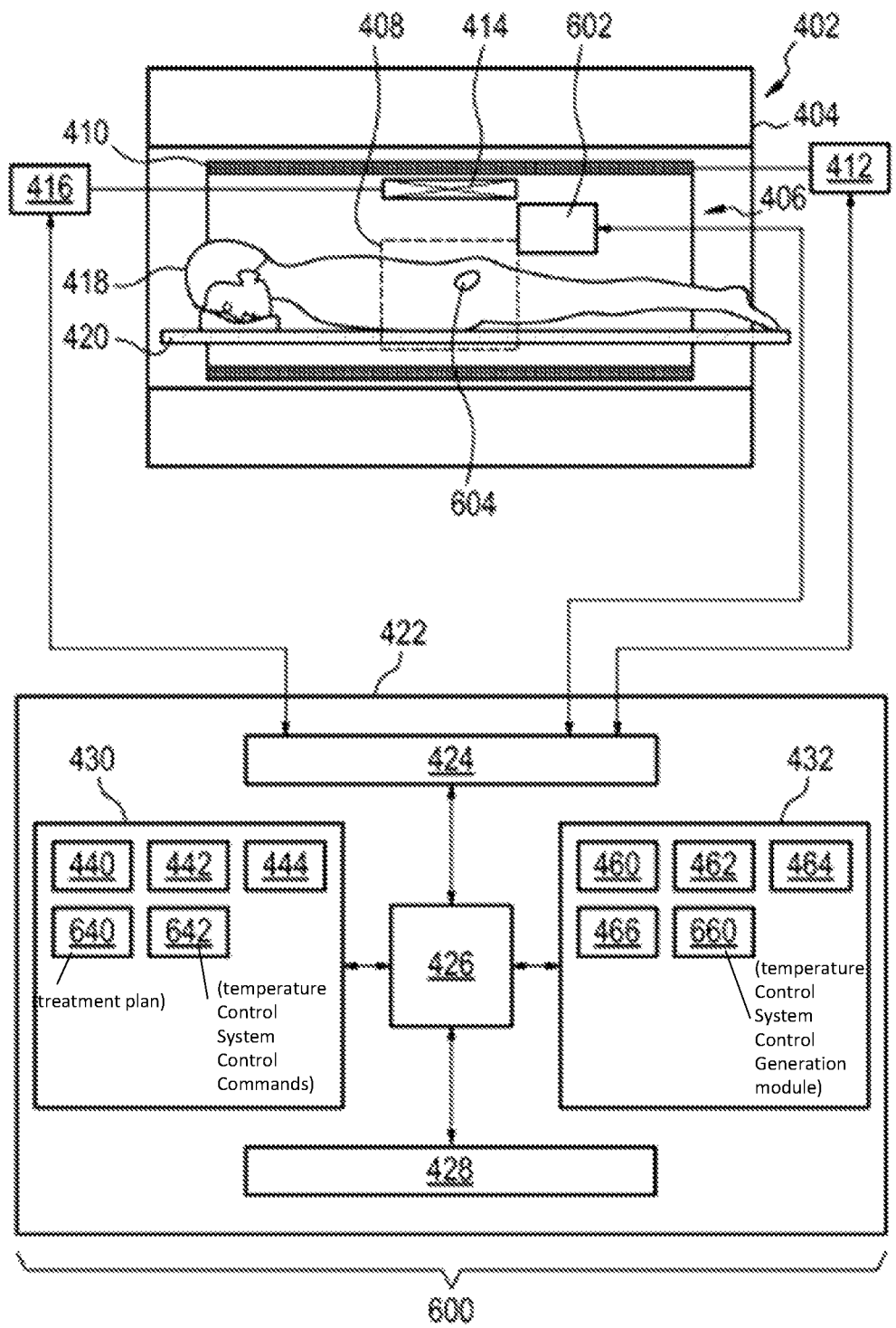
FIG. 6 illustrates a medical apparatus according to a further embodiment of the invention.

FIG. 6 shows a further embodiment of a medical apparatus 600 according to an embodiment of the invention. In this embodiment the medical apparatus 600 is similar to that shown in FIGS. 4 and 5. However, in this case a temperature control system 602 has been incorporated into the medical apparatus 600. The temperature control system may either be a system operable for controllably heating or cooling a portion of a subject.

The temperature control system 602 is connected to the hardware interface 424 of the computer system 422 and is operable for being controlled by the processor 426. The temperature control system 602 in this embodiment is intended to be generic and may represent any system used for heating a portion of a subject. The temperature control system 602 may for instance be, but is not limited to: a high-intensity focused ultrasound system, a radio-frequency temperature control system, a microwave ablation system, a hyperthermia therapy system, a laser ablation system, a cryo-ablation system, and an infrared ablation system. A portion of the subject 418 is indicated as a target zone 604. The temperature control system 602 is able to controllably heat the target zone 604. The computer storage 430 is shown as containing a treatment plan 640. The treatment plan 640 may be descriptive of the internal structure of the subject 418 and contain data which enables identification or location of the target zone 604. Computer storage 430 further contains a set of temperature control system control commands 642 that have been generated using the treatment plan 640. The temperature control system control commands 642 contain commands which enable the processor 426 to control the operation and function of the temperature control system 602.

The computer memory 432 is further shown as containing a temperature control system control generation module 660. The temperature control system control generation module 660 contains computer executable code which enables the processor 426 to generate the temperature control system control commands 642 from the treatment plan 640 and/or the thermal dose estimate 444. Using the thermal dose estimate 444 enables the processor 426 to form a closed control loop for controlling the operation and function of the temperature control system 602.

Figure 7:
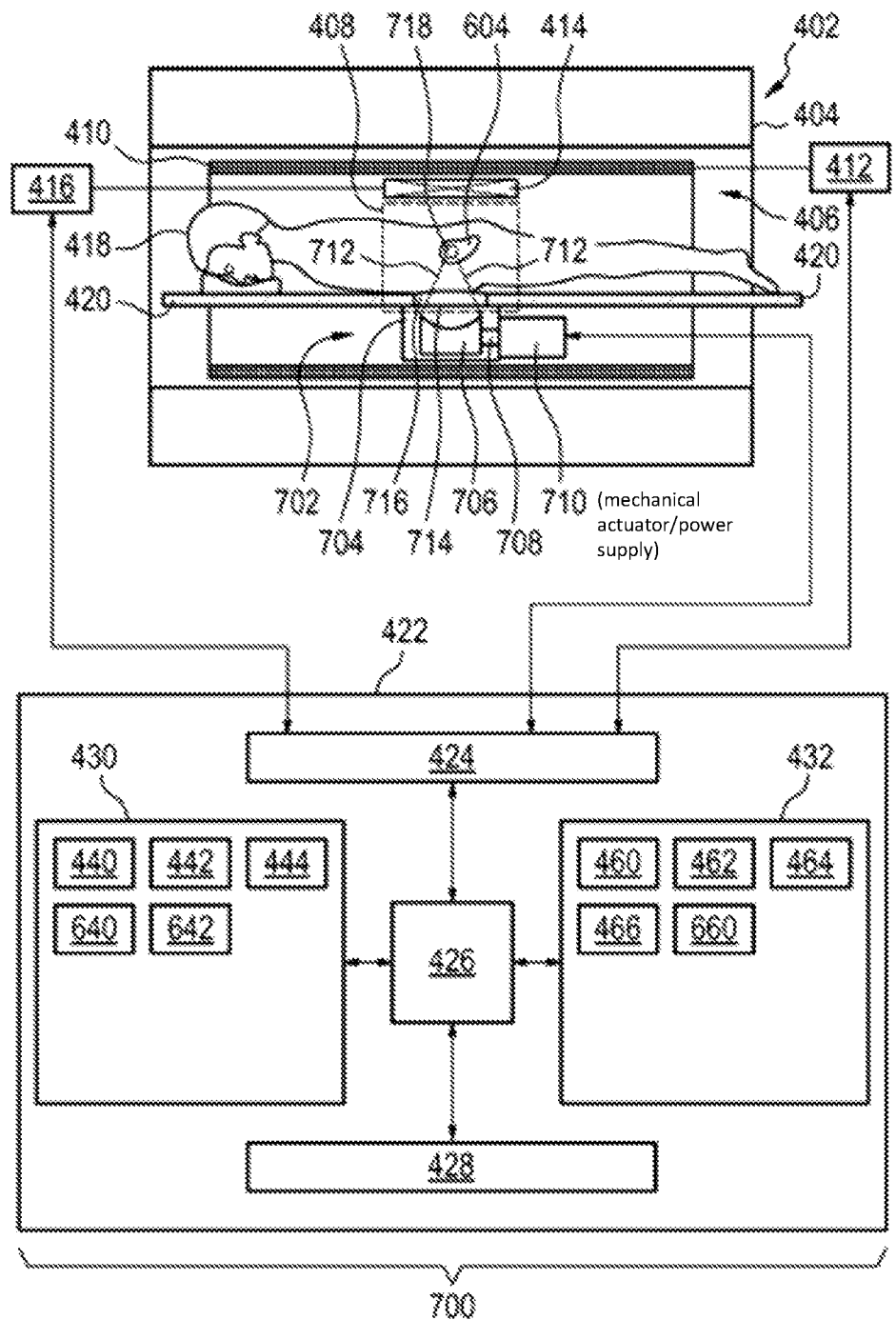
FIG. 7 illustrates a medical apparatus according to a further embodiment of the invention.

FIG. 7 shows a further embodiment of the medical apparatus 700 according to the invention. In this embodiment the temperature control system is a high-intensity focused ultrasound system 702. The high-intensity focused ultrasound system comprises a fluid-filled chamber 704. Within the fluid-filled chamber 704 is an ultrasound transducer 706. Although it is not shown in this Fig. the ultrasound transducer 706 may comprise multiple ultrasound transducer elements each capable of generating an individual beam of ultrasound. This may be used to steer the location of a sonication point 718 electronically by controlling the phase and/or amplitude of alternating electrical current supplied to each of the ultrasound transducer elements. The sonication point 718 is operable to be controlled to sonicate the target zone 604.

The ultrasound transducer 706 is connected to a mechanism 708 which allows the ultrasound transducer 706 to be repositioned mechanically. The mechanism 708 is connected to a mechanical actuator 710 which is adapted for actuating the mechanism 708. The mechanical actuator 710 also represents a power supply for supplying electrical power to the ultrasound transducer 706. In some embodiments the power supply may control the phase and/or amplitude of electrical power to individual ultrasound transducer elements. In some embodiments the mechanical actuator/power supply 710 is located outside of the bore 406 of the magnet 404.

The ultrasound transducer 706 generates ultrasound which is shown as following the path 712. The ultrasound 712 goes through the fluid-filled chamber 704 and through an ultrasound window 714. In this embodiment the ultrasound then passes through a gel pad 716. The gel pad is not necessarily present in all embodiments but in this embodiment there is a recess in the subject support 420 for receiving a gel pad 716. The gel pad 716 helps couple ultrasonic power between the transducer 706 and the subject 418. After passing through the gel pad 716 the ultrasound 712 passes through the subject 418 and is focused to a sonication point 718. The sonication point 718 is being focused within a target zone 604. The sonication point 718 may be moved through a combination of mechanically positioning the ultrasonic transducer 706 and electronically steering the position of the sonication point 718 to treat the entire target zone 604.

The high-intensity focused ultrasound system 702 is shown as being also connected to the hardware interference 424 of the computer system 422. The computer system 422 and the contents of its storage 430 and memory 432 are equivalent to that as shown in FIG. 6.

Figure 8:
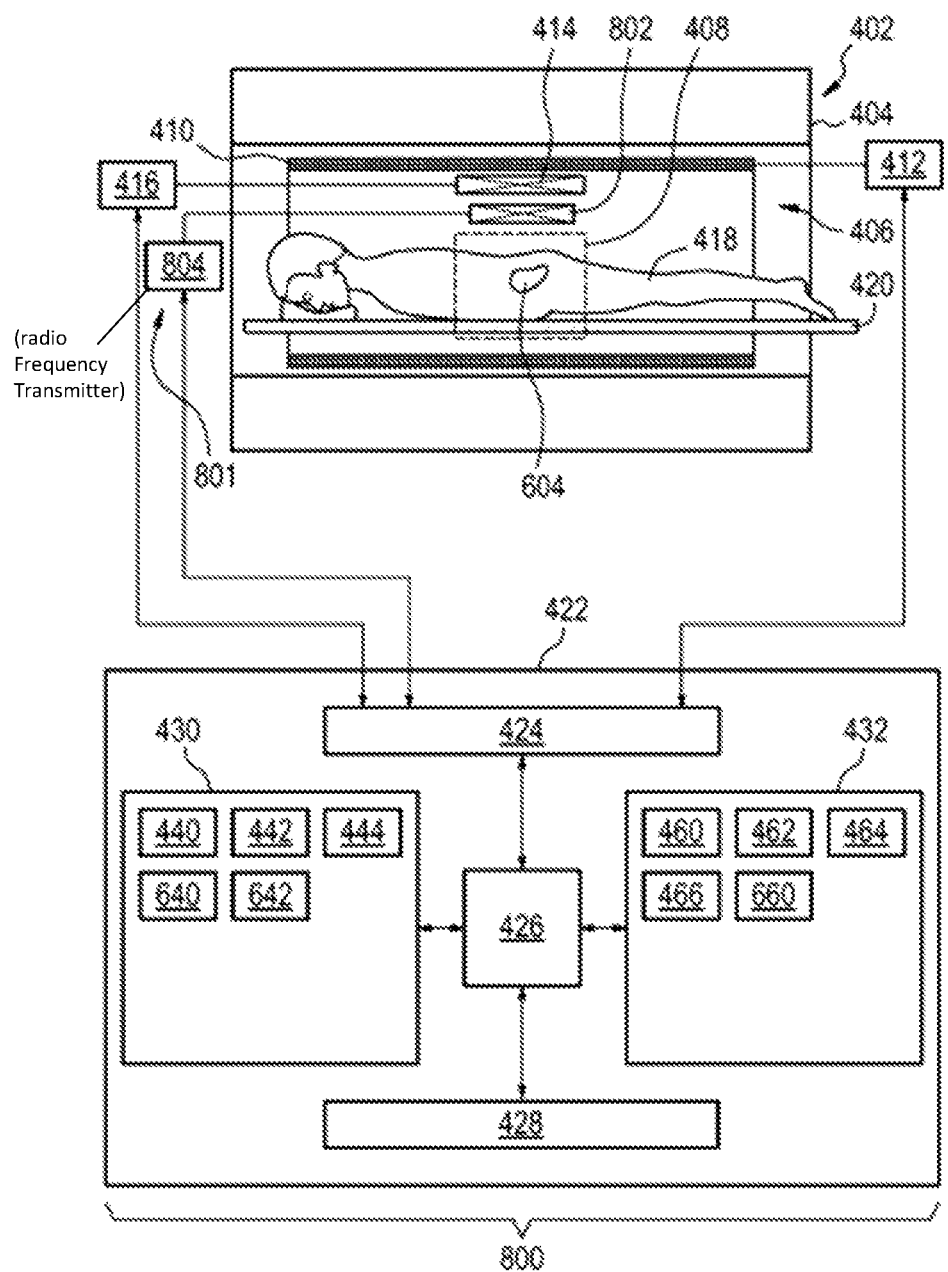
FIG. 8 illustrates a medical apparatus according to a further embodiment of the invention.

FIG. 8 illustrates a medical apparatus 800 according to a further embodiment of the invention. In this embodiment the temperature control system is a radio-frequency temperature control system 801. The embodiment shown in FIG. 8 is similar to that shown in FIG. 6. The computer system 422 of FIG. 8 is equivalent to the computer system 422 shown in FIG. 6. The contents of the computer storage 430 and the computer memory 432 are also equivalent to the computer storage 430 and the computer memory 432 as shown in FIG. 6. In the embodiment shown in FIG. 8 a radio-frequency temperature control system 801 is used as the temperature control system. The radio-frequency temperature control system 801 comprises an antenna 802 and a radio-frequency transmitter 804. The antenna 802 is in the vicinity of target zone 604. Radio-frequency energy generated by the transmitter 804 and radiated by the antenna 802 is used to selectively heat the target zone 604. In this embodiment the radio-frequency transmitter 1004 is shown as being connected to the hardware interface 424. The processor 426 and the contents of the computer storage 430 and the computer memory 432 are used to control the radio-frequency transmitter 804 in a manner equivalent to the way the high-intensity focused ultrasound system 702 of FIG. 7 is controlled by the processor 426.

Figure 9:
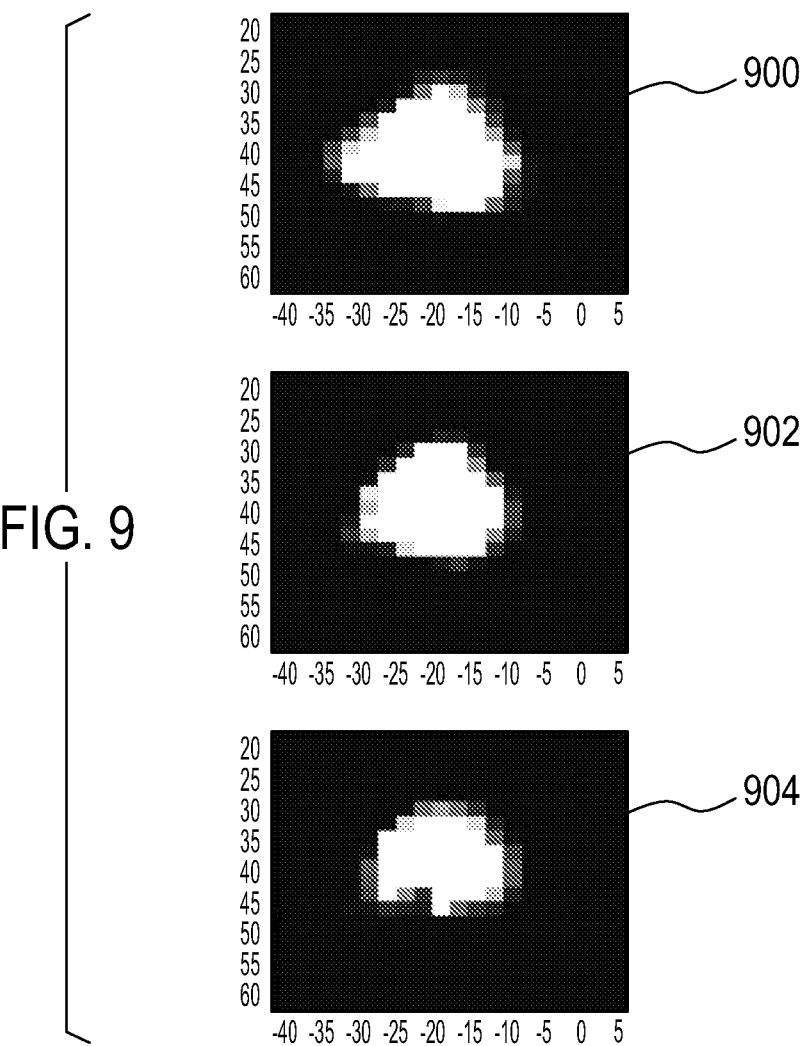
FIG. 9 shows three in vivo thermal dose images perpendicular to the HIFU beam axis after a sonication.

FIG. 9 shows three in vivo thermal dose images from a subject sonication in three parallel coronal slices 900, 902, 904. Slice 902 is between slice 900 and slice 904. In these Figs. white=240 EM thermal dose which is often taken as necrosis in uterine fibroid ablation. Black in the background of the Figs. is 0 thermal dose. The resolution in these images is 2.5×2.5 mm in plane with 7 mm thick slices. There is no gap between the slices 900, 902, 904.

Figure 10:
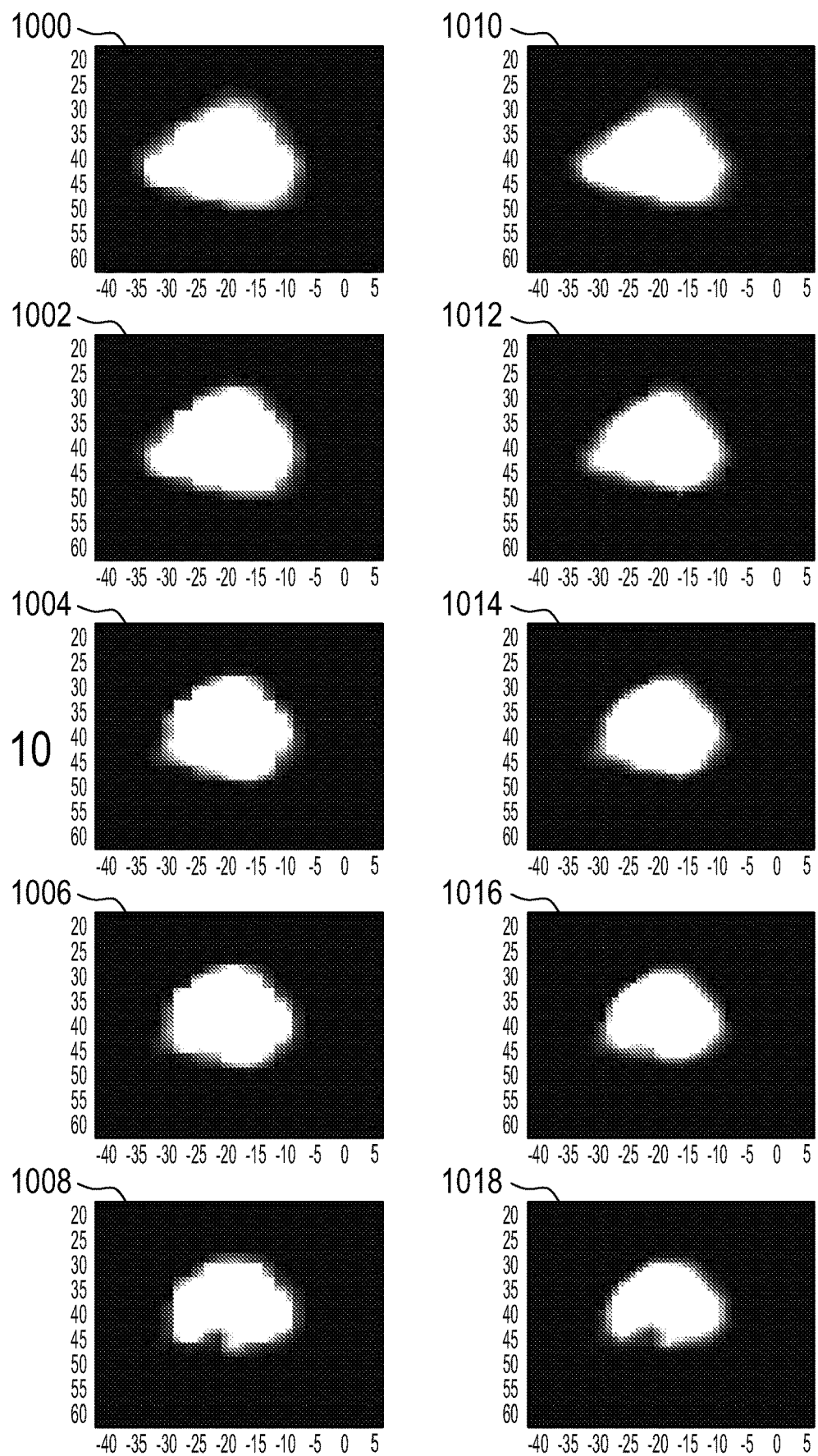
FIG. 10 shows interpolated thermal dose images based on the images shown in FIG. 9.

FIG. 10 shows interpolated thermal dose images based on the images 900, 902, 904 shown in FIG. 9. In FIG. 10 there are ten different images shown. Images 1000, 1002, 1004, 1006, 1008 contain linear interpolation where the dose appears much bulkier and voxel-sized sharp corners can be seen. The images 1010, 1012, 1014, 1016, 1018 contain exponentially interpolated images which seem more natural and smooth. The interpolated resolution is 1×1 mm in slice and is 3.5 mm out of slice. Essentially there is one additional slice added between each of the original slices 900, 902, 904 shown in FIG. 9. Image 900 corresponds to image 1000 and image 1010. Image 902 corresponds to image 1004 and 1014. Image 904 corresponds to image 1008 and image 1018. Image 1002 is the slice between images 900 and 902. Image 1006 is the interpolated image between images 902 and 904. Image 1012 is the interpolated image between 900 and 902. Image 1016 is the interpolated image between 902 and 904.

Figure 11:
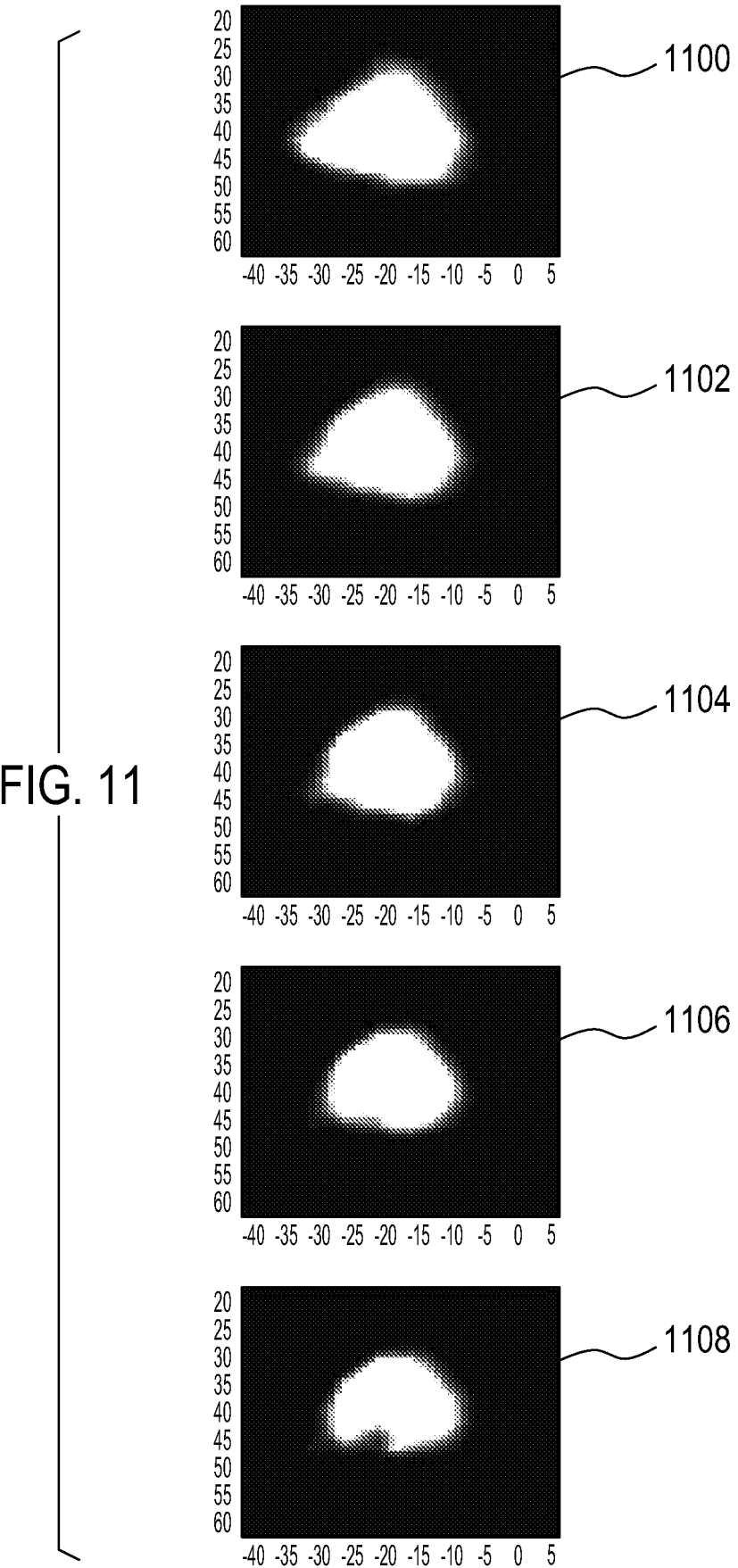
FIG. 11 shows temperature-based interpolation followed by a thermal dose calculation in higher resolution for the same sonication as depicted in FIGS. 9 and 10.

FIG. 11 shows temperature-based interpolation followed by a thermal dose calculation in higher resolution for the same sonication as depicted above in FIGS. 9 and 10. Again in this series there are five images. Image 1100 corresponds to image 900 in FIG. 9. Image 1104 corresponds to image 902. Image 1108 corresponds to image 904. Image 1102 is between image 900 and 902. Image 1106 is between image 902 and 904. The interpolated resolution is 1 mm×1 mm in slice and 3.5 mm out of slice. Essentially as before there is one additional slice between each of the original slices. In these Figs. the order from left to right is from abdomen towards the back of the patient, so called anterior to posterior direction. Visually the differences between FIG. 11 and FIG. 10 are minor. However it is expected that the interpolation shown in FIG. 11 is more accurate than the two interpolations shown in FIG. 10.

Figure 12:
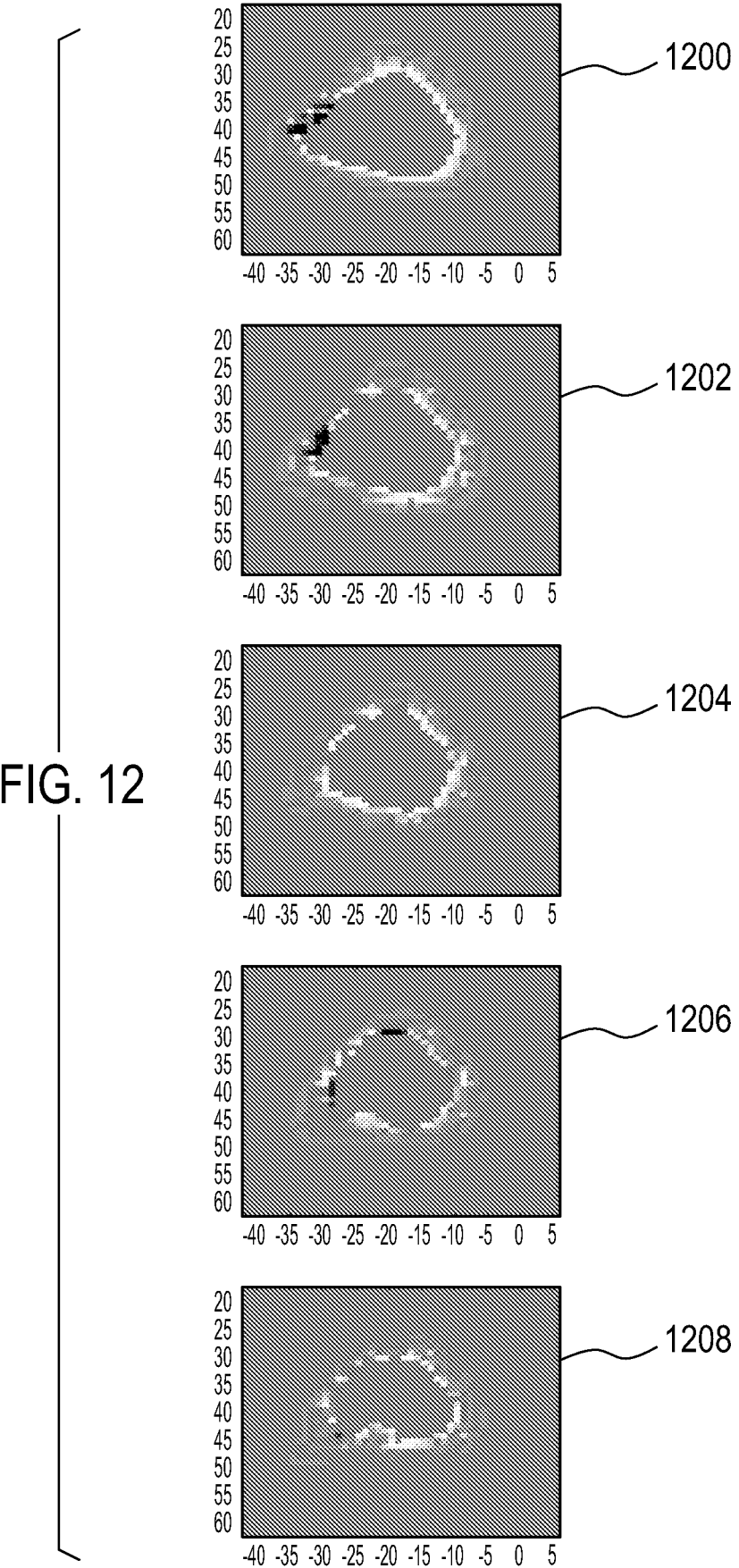
FIG. 12 is a difference image taken between the temperature-based interpolation shown in FIG. 11 versus the exponential dose-based interpolation in the bottom row of FIG. 10.

FIG. 12 shows difference images taken between the temperature-based interpolation shown in FIG. 11 versus the exponential dose-based interpolation in the bottom row of FIG. 10. Image 1200 is a difference between image 1100 and 1010. Image 1202 is a difference between image 1102 and 1012. Image 1204 is a difference between image 1104 and 1014. Image 1206 is a difference between image 1106 and image 1016. Image 1208 is a difference between image 1108 and image 1018. The scale in these images is between −50 to +50 EM. Grey is 0. White is +50 EM and black is −50 EM. Within the region with the thermal dose above 240 EM, the region is masked out for clarity as the exact thermal dose value is not of much interest in this region. It is sufficient to say that the temperature-based interpolation gives a higher dose value both within the 240 EM region as well as on the border. There are only a few pixels where the dose-based interpolation gives a higher value. These are the dark grey voxels with the level of darkness representing the magnitude in the difference.

The linear dose interpolation in the top row, images 1000 through 1008, of FIG. 10 is done in 1D as follows:

$$D_{int} = D_0 * (1-x) + D_1 * x \quad [1]$$

where $D_0$ and $D_1$ are the thermal dose in two points and x is the distance in normalized coordinates from $D_1$ to the interpolation point $D_{int}$, with the thermal dose obtained from the temperature as $$D_j = \sum_i r^{43-T_j(i)} dt_i \quad [2]$$

where the subscript j is added for clarity and corresponds to the subscript of zero or one in equation 1 and 3.

The exponential dose interpolation in the bottom row, images 1010 through 1018, of FIG. 10 is done based on the insight that the temperature between two points at a small distance tends to be smooth and a linear interpolation is then a good approximation as well as the fact that the thermal dose is an exponential equation with the temperature in the exponent (proof below). The similar interpolation using the same denomination as above is then done using:

$$D_{int} = [D_0]^{1-x} * [D_1]^x \quad [3]$$

The higher resolution thermal dose interpolation in FIG. 11 is obtained using the interpolation of the temperature and then calculating a thermal dose based on this interpolated temperature. So in a first step an interpolated temperature image is calculated by linear interpolation at each and every time point when a temperature image was acquired in the same way as for the dose in equation 1 above. In the second step, this interpolated temperature is then used to calculate the interpolated dose:

$$D_{int} = \sum_i r^{43-T_{int}(i)} dt_i \quad [4]$$

The direct interpolation of the thermal dose based on the thermal dose maps (as in FIG. 10) that are obtained at the end of temperature monitoring for a given sonication is less computationally expensive than the interpolation of the temperature images at each and every dynamic level. The difference in computational burden is not large as linear interpolation is always very straightforward.

The interpolations methods are now discussed in more detail. The thermal dose will be calculated as:

$$D = \sum_i r^{43-T(i)} dt_i = \sum_i d(i) * dt_i \quad [5]$$

The first interpolation method is a simple linear interpolation:

$$D_{int} = D_0 * (1-x) + D_1 * x, \quad [6]$$

where $D_0$ and $D_1$ are the thermal doses at point zero and one, respectively, between which the interpolated point is situated at a normalized distance x from point zero. The second interpolation method is an exponential interpolation:

$$D_{int} = [D_0]^{1-x} * [D_1]^x \quad [7]$$

The reasoning behind this is that if we can consider the voxel temperature to be a sparsely sampled version of the real temperature, then the temperature between these sparsely sampled points can be assumed with reasonable accuracy to be a linear interpolation as all higher order fluctuations should even out trough diffusion. This is of course assuming that the ratio of the diffusion and voxel resolution is sufficiently large that persistent higher order temperature variations are impossible. If this is the case the thermal dose can be calculated as $$D_{int} = \sum_i r^{43-T_{int}(i)} dt_i \quad [8]$$

$$= \sum_i r^{43-(T_0(i)*(1-x)+T_1(i)*x)} dt_i$$

$$= \sum_i r^{43-T_0(i)*(1-x)-43*x} r^{43*x-T_1(i)*x} dt_i$$

$$= \sum_i r^{[43-T_0(i)]*(1-x)} r^{[43-T_1(i)]*x} dt_i$$

$$= \sum_i d_0(i)^{(1-x)} d_1(i)^x dt_i$$

However, this is not the same as in Eq. 7 as the exponential interpolation in Eq. 8 is per instance of time and then summed instead of exponentially interpolating the sums as is the case in Eq. 7.

When estimating thermal doses it may be beneficial to have an estimate of the thermal damage in 3D at a fairly high resolution. Moreover, if more than one heating is performed then the thermal damage inflicted by the individual heatings should preferably be put into the same frame of reference so that the total thermal damage inflicted for the entire heating or cooling session can be assessed in 3D. This estimate can then be overlaid for example on anatomical 3D magnetic resonance (MR) images, and then be used to provide an endpoint by simply estimating when the thermal dose in the target region has reached a sufficient level. Moreover, this may be used for assessing the thermal dose near sensitive structures or near the border of the target region.

Once the 3D thermal dose is determined and updated, MPRs may beneficially be used in any plane for the visualization thus making the computational burden low. Moreover, the imaging planes need not be planar but can also be curved to follow the border of a sensitive structure such as for example the skin in breast HIFU therapy.

Provided the temperature measurements are available the problem is how to transfer the temperature data obtained in some 2D planes to a 3D volume of common reference in a reliable and representative manner. The text below will focus on heating applied by externally placed HIFU transducers, although it is also applicable to other HIFU transducers such as transurethral catheters for prostate HIFU for example with some trivial modifications. If several heating events are performed at different positions for other thermal therapies under temperature monitoring then the same solution may also applied there.

Commonly, the 2D imaging planes containing the temperature maps have a fairly low resolution (e.g. 2.5×2.5×7 mm³ for the Sonalleve uterine fibroid application) which is required to obtain the MR temperature maps sufficiently fast. The 3D volume containing the thermal dose estimate needs to be of a higher resolution in order for several heating events to be correctly represented in this frame of reference. The smoothness of the temperature may be utilized to this end since any sharp corners will be smoothened by inherent thermal diffusion.

Embodiments of the invention may provide a means of obtaining a 3D thermal dose estimate representative of the underlying tissue thermal damage estimate. One feature may be a means of reliably interpolating the temperature information obtained from the thermometry to a higher resolution and using the shape of the heating, which is known or can be estimated, to estimate the thermal dose of the heated 3D volume at a higher resolution for any given heating event. The high resolution interpolated 3D thermal dose of all heating events may then be added to the same 3D high resolution frame of reference. This allows for estimating the total thermal damage in 3D of the entire session, thus enabling an improved visualization of the thermal damage estimate for the clinician that may in turn make the thermal dose to be a more accurate therapeutic endpoint. The safety may also be improved as a consequence since the accumulated thermal damage at the borders and outside of the target area is better visualized.

If the temperature images are available when calculating the 3D dose, then a linear interpolation of the temperature images to a higher resolution is one approach. Alternatively, an exponential interpolation of the low-resolution acquired thermal dose images to the higher resolution common reference is also acceptable. In some embodiments, this may require a one-step calculation at the end of each heating event rather than an additional calculation during heating, which may be beneficial to reduce the computational burden during heating. However, this alternative tends to be less accurate. It may be that also in vivo calculating the center of mass and using that as a center-point for the higher resolution images provides a thermal dose that is more representative of the actual underlying thermal dose. This is at least the case in phantom experiments. Also, the higher the original spatial resolution is the better the interpolation will be. Moreover, for heating events that only heat up small areas on the scale of a voxel, the interpolation will not be accurate.

In order to obtain an estimate in 3D several imaging planes are needed, either parallel or not. If the sampled volume is a 3D thermal map then this step is naturally not needed. If the temperature is only measured in discrete points then this will necessarily cause the 3D dose estimate to be less reliable. The larger the part of the heated area that has a temperature measured, the more reliable the 3D dose estimate will be. In the areas where no temperature is measured, the symmetry of the heat source and heating and/or the Pennes' bioheat equation may be used to obtain estimates of what the temperature is likely to be in those areas. For example, in the case of HIFU sonication with external transducers the heating is likely to be axially symmetric due to the shape of the ultrasound intensity field as long as the tissue is sufficiently homogeneous.

If there are areas with more than one observation, for example in the area with intersecting coronal and sagittal MR temperature images, then all observations may be used in the interpolation.

In one embodiment, a location in 3D is given to each voxel in all planes imaged that has a temperature estimate and then this is interpolated to one high resolution 3D dose estimate in one step. In a second embodiment, the interpolation to a higher resolution is first done for each stack of parallel slices separately. Then the shape of the heating is utilized and possible cross-sections of the stacks are dealt with. Alternatively, the interpolation may in this case be first for each slice only and in-plane before the second step.

Finally, some masking based on the reliability of the temperature estimates (e.g. SNR in MR thermometry) and/or the location of the intended heating is likely to be beneficial to avoid noise coming into the thermal dose 3D estimate.

In some embodiments, multiple observations of the temperature are first needed. For MR thermometry, this typically means several imaging slices or planes. These may be parallel or perpendicular.

All available information may be used, meaning if there are intersecting areas then all of the observations from these areas should be used. If possible it is also preferred to account for possible partial volume effects if the underlying shape of the heating source e.g. the HIFU focus is known or can be reliably estimated or symmetry may be utilized. This may be the case if acoustic simulations can be applied.

In particular, in areas where the heating is only partially sampled the underlying heat source shape and/or symmetry of the heating may be beneficial to use. In case of larger heated areas per sonication (so-called large treatment cells), some of the tissue heated may extend in the beam path direction, i.e. the AP direction, beyond the coronal slices. In such an event, only the tissue within the sagittal slice is sampled in those areas. Tissue situated sufficiently far away from the beam-axis in the LR direction will not be sampled. However, assuming smoothness of the temperature and a fairly rotationally symmetric beam path one can get an educated guess of the temperature in those regions as well.

One problem in combining the intersecting slices is that the voxels seldom have the same 3D coordinates but may yet have different values due to partial volume effects and noise. One simple way of taking into account the overlapping data is to first interpolate the sagittal slice in this example to a somewhat higher but still coarse in-plane resolution and also interpolate the coronal stack in 3D to the same resolution. The AP resolution of the interpolated coronal stack should equal the in-plane AP resolution of the interpolated sagittal slice. The FH resolutions should also match. For simplicity, the resolution may be isotropic. Interpolating this data set to a higher resolution still would then take the intersecting data fully into account. This way the temperature data can be utilized. Another option where only the thermal dose contours is utilized is to use standard approaches to tracing a 3D object from intersecting 2D planes. Such tools exist, and often rely on the use of Bezier curves.

To avoid the effect of artifacts and noise making the interpolation complicated, it is preferable to mask out all areas known not to be heated. This makes the 3D dose calculation quicker and less susceptible to errors. This approach is fully acceptable since this is only meant for visualization.

Once the thermal dose 3D estimate is obtained, it is added to the common 3D volume for the cumulative thermal dose estimate. This volume which is preferable of isotropic and high resolution can then be rapidly and easily accessed by the therapy control software and the thermal dose can be displayed in any direction using for example MPR. Curved slices may also be visualized if so is desired, for example at the surface of organs at risk (OARs) such as the skin bowels etc. Interpreting the thermal dose in planar slices that cross-sect the OAR at different positions is often difficult, and curved slices enabled by the high-resolution 3D cumulative thermal dose may provide an advantage.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 400 medical apparatus
402 magnetic resonance imaging system
404 magnet
406 bore of magnet
408 imaging zone
410 magnetic field gradient coil
412 magnetic field gradient coil power supply
414 radio frequency coil
416 radio frequency transceiver
418 subject
420 subject support
421 slice
421' slice
421" slice
422 computer system
424 hardware interface
426 processor
428 user interface
430 computer storage
432 computer memory
440 pulse sequence
442 magnetic resonance thermometry data
444 3D thermal dose estimate
460 control module
462 magnetic resonance data image reconstruction module
464 interpolation module
466 thermal dose calculation module
500 medical apparatus
502 two dimensional thermal doses
504 interpolated three dimensional thermal maps
506 second 3D thermal dose estimate
508 cumulative 3D thermal dose estimate
510 dose estimate summing module
600 medical apparatus
602 temperature control system
604 target zone
640 treatment plan
642 temperature control system control commands
660 temperature control system control generation module
700 medical apparatus
702 high intensity focused ultrasound system
704 fluid filled chamber
706 ultrasound transducer
708 mechanism
710 mechanical actuator/power supply
712 path of ultrasound
714 ultrasound window
716 gel pad
718 sonication point
800 medical apparatus
801 radio-frequency temperature control system
802 antenna
804 radio-frequency transmitter
900 in vivo thermal dose image
902 in vivo thermal dose image
904 in vivo thermal dose image
1000 linearly interpolated thermal dose image
1002 linearly interpolated thermal dose image
1004 linearly interpolated thermal dose image
1006 linearly interpolated thermal dose image
1008 linearly interpolated thermal dose image
1010 exponentially interpolated thermal dose image
1012 exponentially interpolated thermal dose image
1014 exponentially interpolated thermal dose image
1016 exponentially interpolated thermal dose image
1018 exponentially interpolated thermal dose image
1100 thermal dose image calculated from temperature interpolation

1102 thermal dose image calculated from temperature interpolation
1104 thermal dose image calculated from temperature interpolation
1106 thermal dose image calculated from temperature interpolation
1108 thermal dose image calculated from temperature interpolation
1200 difference image between images 1100 and 1010
1202 difference image between images 1102 and 1012
1204 difference image between images 1104 and 1014
1206 difference image between images 1106 and 1016
1208 difference image between images 1108 and 1018

The invention claimed is:

1. A medical apparatus comprising:
a magnetic resonance imaging system for acquiring magnetic resonance thermometry data from a subject, wherein the magnetic resonance imaging system comprises a magnet with an imaging zone;
a temperature control system operable for controlling the temperature within a target zone located within the imaging zone;
a memory for storing machine executable instructions;
a processor for controlling the medical apparatus, wherein execution of the machine executable instructions causes the processor to:
acquire the magnetic resonance thermometry data from multiple slices within the imaging zone by controlling the magnetic resonance imaging system;
interpolate a three dimensional thermal dose estimate in accordance with the magnetic resonance thermometry data;
receive a treatment plan; and
control the temperature control system in accordance with the treatment plan to control the temperature within the target zone;
wherein the instructions cause the processor to acquire at least part of the magnetic resonance thermometry data when controlling the temperature control system,
wherein the target zone has a border, wherein execution of the instructions further causes the processor to calculate a border thermal dose within a predetermined distance from at least a portion of the border.

2. The medical apparatus of claim 1, wherein the three dimensional thermal dose estimate has a higher spatial resolution than the magnetic resonance thermometry data.

3. The medical apparatus of claim 1, wherein execution of the instructions further cause the processor to modify the treatment plan in accordance with the three dimensional thermal dose estimate.

4. The medical apparatus of claim 1, wherein execution of the instructions further cause the processor to:
detect an endpoint condition using the three dimensional thermal dose estimate and the treatment plan; and
halt at least a portion of the temperature control of the target zone by sending a halt command to the temperature control system if the endpoint condition is detected.

5. The medical apparatus of claim 1, wherein execution of the instructions further cause the processor to determine a heating center of mass using the treatment plan, and wherein the interpolating the three dimensional thermal dose estimate is interpolated at least partially using the heating center of mass.

6. The medical apparatus of claim 1, wherein execution of the instructions further cause the processor to determine a heating trajectory using the treatment plan, and wherein the interpolating the three dimensional thermal dose estimate is interpolated at least partially using the heating trajectory.

7. The medical apparatus of claim 1, wherein the temperature control system is any one of the following: high intensity focused ultrasound, radio-frequency temperature control system, a microwave ablation system, a hyperthermia therapy system, a laser ablation system, an infrared ablation system, and a cryo-ablation system.

8. The medical apparatus of claim 1, wherein the execution of the machine executable instructions causes the processor to interpolate the three dimensional thermal dose estimate in accordance with the magnetic resonance thermometry data by one of:
linear interpolation of the magnetic resonance thermometry data followed by conversion of the interpolated magnetic resonance thermometry data to interpolated thermal dose data; or
conversion of the magnetic resonance thermometry data to thermal dose data followed by exponential interpolation of the thermal dose data.

9. A non-transitory computer readable medium storing machine executable instructions for execution by a processor controlling a medical apparatus, wherein the medical apparatus comprises a magnetic resonance imaging system for acquiring magnetic resonance thermometry data from a subject, wherein the magnetic resonance imaging system comprises a magnet with an imaging zone, wherein execution of the machine executable instructions causes the processor to:
acquire the magnetic resonance thermometry data from multiple slices within the imaging zone by controlling the magnetic resonance imaging system;
interpolate a three dimensional thermal dose estimate in accordance with the magnetic resonance thermometry data by linear interpolation of the magnetic resonance thermometry data followed by conversion of the interpolated magnetic resonance thermometry data to interpolated thermal dose data; and
controlling a temperature control system of the medical apparatus to control the temperature within a target zone using the three dimensional thermal dose estimate for closed loop control.

10. The non-transitory computer readable medium of claim 9, wherein the controlling comprises:
receiving a treatment plan; and
controlling the temperature control system in accordance with the treatment plan to control the temperature within the target zone,
wherein the instructions cause the processor to acquire at least part of the magnetic resonance thermometry data when controlling the temperature control system.

11. The non-transitory computer readable medium of claim 10, wherein execution of the instructions further cause the processor to:
modify the treatment plan in accordance with the three dimensional thermal dose estimate.

12. The non-transitory computer readable medium of claim 10, wherein execution of the instructions further cause the processor to:
detect an endpoint condition using the three dimensional thermal dose estimate and the treatment plan; and
halt at least a portion of the temperature control of the target zone by sending a halt command to the temperature control system if the endpoint condition is detected.

13. A method of controlling a medical apparatus, wherein the medical apparatus comprises a magnetic resonance imaging system for acquiring magnetic resonance thermometry data from a subject, wherein the magnetic resonance imaging system comprises a magnet with an imaging zone, wherein the method comprising:

acquiring the magnetic resonance thermometry data from multiple slices within the imaging zone by controlling the magnetic resonance imaging system;

interpolating a three dimensional thermal dose estimate in accordance with the magnetic resonance thermometry data by conversion of the magnetic resonance thermometry data to thermal dose data followed by exponential interpolation of the thermal dose data; and controlling a temperature control system of the medical apparatus to control the temperature within a target zone using the three dimensional thermal dose estimate for closed loop control.

14. The method of claim 13, further including:

receiving a treatment plan; and controlling the temperature control system in accordance with the treatment plan to control the temperature within the target zone; and wherein the instructions cause the processor to acquire at least part of the magnetic resonance thermometry data when controlling the temperature control system.

15. The method of claim 14, wherein the method further includes:

modifying the treatment plan in accordance with the three dimensional thermal dose estimate.

\* \* \* \* \*